United States Patent [19]
Abele et al.

[11] Patent Number: 5,103,804
[45] Date of Patent: Apr. 14, 1992

[54] EXPANDABLE TIP HEMOSTATIC PROBES AND THE LIKE

[75] Inventors: John E. Abele, Concord, Mass.; Charles E. Lennox, Hudson, N.H.

[73] Assignee: Boston Scientific Corporation, Watertown, Mass.

[21] Appl. No.: 547,939

[22] Filed: Jul. 3, 1990

[51] Int. Cl.⁵ .............................................. A61B 1/00
[52] U.S. Cl. ..................................... 128/4; 128/401; 604/114; 604/291
[58] Field of Search .................. 128/4, 6, 399, 400, 128/401, 402; 604/113, 114, 291

[56] References Cited

U.S. PATENT DOCUMENTS

| | | | |
|---|---|---|---|
| 612,724 | 10/1898 | Hamilton . | |
| 2,032,859 | 3/1936 | Wappler | 174/89 |
| 2,043,083 | 6/1936 | Wappler | 128/303.11 |
| 2,078,686 | 7/1935 | Rowe | 128/255 |
| 2,126,070 | 8/1938 | Wappler | 128/172.1 |
| 3,858,577 | 1/1975 | Bass et al. | 128/8 |
| 3,858,586 | 1/1975 | Lessen | 128/303.1 |
| 3,900,022 | 8/1975 | Wildran | 128/7 |
| 3,920,021 | 1/1975 | Hilterbrandt | 128/303.17 |
| 4,003,380 | 1/1977 | Wien | 128/303.17 |
| 4,011,872 | 3/1977 | Komiya | 128/303.14 |
| 4,315,512 | 2/1982 | Fogarty | 128/344 |
| 4,324,262 | 4/1982 | Hall | 128/756 |
| 4,445,892 | 5/1984 | Hussein et al. | 604/101 |
| 4,449,528 | 5/1984 | Auth et al. | 128/303.1 |
| 4,470,407 | 9/1984 | Hussein | 128/6 |
| 4,522,194 | 6/1985 | Normann | 128/1 D |
| 4,532,924 | 8/1985 | Auth et al. | 128/303.17 |
| 4,582,057 | 4/1986 | Auth et al. | 128/303.1 |
| 4,583,526 | 4/1986 | Ali | 128/6 |
| 4,641,649 | 2/1987 | Walinsky et al. | 128/303.1 |
| 4,643,186 | 2/1987 | Rosen et al. | 128/303.1 |
| 4,646,737 | 3/1987 | Hussein et al. | 128/303.1 |
| 4,648,893 | 3/1987 | Kittrell et al. | 65/4.21 |
| 4,662,368 | 5/1987 | Hussein et al. | 128/303.1 |
| 4,662,383 | 5/1987 | Sogawa et al. | 128/784 |
| 4,669,467 | 6/1987 | Willett et al. | 128/303.1 |
| 4,696,668 | 9/1987 | Wilcox | 604/268 |
| 4,709,698 | 12/1987 | Johnston et al. | 128/303.12 |
| 4,717,387 | 1/1988 | Inoue et al. | 604/264 |
| 4,718,417 | 1/1988 | Kittrell et al. | 128/303.1 |
| 4,754,752 | 7/1988 | Ginsburg et al. | 128/303.12 |
| 4,867,874 | 9/1989 | Kellner | 128/6 |
| 4,955,377 | 9/1990 | Lennex et al. | 128/401 |

FOREIGN PATENT DOCUMENTS

| | | |
|---|---|---|
| 0182689 | 5/1986 | European Pat. Off. . |
| 718993 | 1/1932 | France ........... 12/6 |
| 8200768 | 3/1982 | PCT Int'l Appl. . |
| 8303188 | 9/1983 | PCT Int'l Appl. . |
| 9004365 | 5/1990 | PCT Int'l Appl. . |

OTHER PUBLICATIONS

American Cystoscope Makers, Inc., "ACMI Bipolar Hemostatic Electrode," Dec. 12, 1980.

(List continued on next page.)

*Primary Examiner*—William H. Grieb
*Attorney, Agent, or Firm*—Fish & Richardson

[57] ABSTRACT

Device and method for treating tissue inside a patient's body, the device including an endoscopically introducible catheter shaft. The endoscope is constructed for insertion into the patient's body, and has a channel passing through it. The channel terminates at an opening in the distal end of the endoscope. The channel enables the catheter shaft to pass through the endoscope and beyond the distal end of the endoscope. A chamber is mounted on the catheter shaft. The chamber is defined by a flexible wall. The chamber is associated with a first lumen defined by the catheter for fluid flow between the chamber and a fluid source outside of the patient's body. The chamber is fillable with fluid after placement in the patient's body. When the chamber is filled with fluid it has a diameter greater than the diameter of the transverse cross-section of the endoscope channel. According to the method, the endoscope is inserted into a patient's body and is used to view the inside of the patient's body, to determine the location of tissue to be treated. The catheter is inserted into the channel that passes through the endoscope. The chamber is filled with fluid and is positioned at the location of tissue to be treated.

19 Claims, 6 Drawing Sheets

OTHER PUBLICATIONS

American Cystoscope Makers, Inc., "BICAP Hemostatic System," Jul., 1984.
Auth, "Endoscopic Heat Probe Coagulation," Olympus Corporation, date unknown.
Gilbert et al., "Nonsurgical Management of Acute Nonvariceal Upper Gastrointestinal Bleeding," *Progress in Hemostasis and Thrombosis,* vol. 4, Grune & Stratton, 1987.
Katzir, "Optical Fibers in Medicine," Sep. 24, 1985.
Litvack et al., "Angioscopic Visualization of Blood Vessel Interior in Animals and Humans," Clinical Cardiology Publishing Co., Inc. 1985.
Luxtron Corp., "Small Business Innovation Research Program," 1984.
Moore et al., "Evaluation of Bipolar Electrocoagulation in Canine Stomachs," Gastrointestinal Endoscopy, vol. 24, No. 4, 1987.
Protell et al., "Computer-Assisted Electrocoagulation: Bipolar vs. Monopolar in the Treatment of Experimental Gastric Ulcer Bleeding," American Gastroenterological Association, May 21-23, 1979.
Protell et al., "The Heater Probe: A New Endoscopic Method for Stopping Massive Gastrointestinal Bleeding," Gastroenterology, vol. 74, American Gastroeneterological Association, 1978.
Silverstein et al., "Development and Testing of a Gas-Jet-Assisted Argon Laser Waveguide," Gastroenterology, vol. 74, No. 1, American Gastroenterological Association, May 22-25, 1978.
Ward, "Laser Recannalization of Atheromatous Vessels Using Fiber Optics," Alan R. Lisa, Inc., 1984.
Zeither et al., "A Prototype RF-Heated 'Hot Balloon' PTCA-Catheter: Design Parameters and in Vitro Tissue Studies," Circulation Supplement, American Heart Association, Nov. 14-17, 1988.

EXPANDABLE TIP HEMOSTATIC PROBES AND THE LIKE

BACKGROUND OF THE INVENTION

This invention relates to endoscopic devices and the like for treating tissue inside a patient's body, e.g., hemostatic probes, insertable through an endoscope, for applying heat to an ulcer or other internal lesion.

A hemostatic probe can include a catheter constructed for insertion through a channel in an endoscope. The channel terminates in an opening at the distal end of the endoscope. The endoscope is first inserted into a duct in the patient's body, and is used for internal viewing, to determine the location of a lesion. The lesion may be, for example, a disruption of the mucosa of the stomach or a bleeding stomach ulcer. The catheter is then inserted through the channel in the endoscope. The catheter has a heating device on its distal end. The heating device is pressed against the location of the lesion, and heat is applied to the lesion. The combination of heat and pressure causes coagulation at the lesion.

SUMMARY OF THE INVENTION

In one aspect, the invention features an endoscopically introducible, heatable probe for engagement with and heating treatment of body tissue on the basis of thermal conduction. The probe is sized and constructed for insertion into the body of a patient through a channel of an endoscope. The probe includes a catheter shaft that defines a liquid filling lumen. A thin-walled, collapsible liquid inflatable chamber at the distal end of the catheter shaft is in liquid receiving relationship with the filling lumen. The catheter, with the chamber-defining wall in collapsed condition, is sized to pass through the channel of the endoscope. The chamber has an inflated diameter that is greater than the diameter of the transverse cross-section of the endoscope channel. A heating device maintains inflation liquid in the chamber at a predetermined elevated tissue-treating temperature. The probe, when the chamber is deflated, can be inserted into the body through the endoscope and thereafter the chamber can be inflated with liquid, the liquid can be heated, and the chamber can be pressed against tissue to treat a relatively large area of the tissue.

In preferred embodiments, the heating device is located within the chamber, and causes electrical current to flow through the liquid within the chamber to heat the liquid on the basis of I²R losses of the electrical current flowing through the liquid. The liquid in turn heats surrounding tissue by thermal conduction through the wall of the chamber. The heating device includes a plurality of spaced electrical contacts enclosed within the chamber and exposed to the fluid within the chamber. The heating means further includes a corresponding plurality of conductors for connecting the electrical contacts to a power supply that applies a radio frequency electrical potential to the contacts. The liquid is an electrically conductive liquid preselected to produce resistive heating. The radio frequency electrical potential causes current to flow through the liquid between the contacts. The chamber and the contacts are cooperatively constructed and arranged to cause the current to be substantially confined to liquid within the chamber.

In one embodiment, the chamber is a balloon that surrounds the distal end of the catheter shaft, and that extends axially beyond the distal end of the catheter shaft when the balloon is inflated.

In another embodiment, the chamber is a balloon that is disposed annularly around the distal portion of the catheter shaft in a manner such that, when filled with the liquid, the chamber extends distally beyond the end of the catheter shaft. The catheter shaft defines a lumen that extending through the catheter shaft and terminates at an opening in a distal end of the catheter shaft. A guidewire may pass through the lumen of the catheter shaft, in order to facilitate introduction of the catheter shaft through the channel of the endoscope.

The chamber may be an elastic balloon or a foldable, substantially noncompliant balloon. The predetermined temperature that is sufficient to cause coagulation may be a boiling temperature of the liquid within the chamber.

In another aspect, the invention features a method of treating tissue inside a patient's body. A user inserts an endoscope into the patient's body. A channel passes through the endoscope and terminates at an opening in a distal end of the endoscope. The user views the inside of the patient's body through the endoscope, to determine the location of tissue to be treated, and inserts a catheter shaft into the channel, in a manner such that a portion of the catheter shaft extends beyond the opening in the distal end of the endoscope. A chamber, defined by a flexible wall, is mounted on the portion of the catheter shaft that extends beyond the opening in the distal end of the endoscope. The user fills the chamber with fluid, to cause the chamber to expand to a diameter greater than the transverse cross-section of the endoscope channel, and positions the chamber at the location of tissue to be treated.

The user may direct the chamber in an axial direction or a tangential direction to the location of the tissue to be treated, and may apply pressure to the tissue as the tissue is heated, so that the tissue is compressed, thereby minimizing heat sinking of the tissue.

Hemostatic probes according to the invention can apply heat tangentially as well as en face, and can conform to the shape of the surface to which heat is being applied, to compress the tissue evenly and provide uniform heat transfer. Since the area of contact between the chamber and the tissue that is treated is relatively large, it is not necessary to reposition the chamber at multiple locations to ensure that an entire lesion is treated. Even if the user positions the probe somewhat off-center with respect to the lesion, the probe can nevertheless cause coagulation of bleeding arteries in the range of a millimeter in diameter. Hemostatic probes according to the invention can be used with relatively small endoscopes, because the chamber at the tip of the hemostatic probe expands to a diameter greater than the diameter of the transverse cross-section of the endoscope channel. Thus, it is not necessary to switch to a larger endoscope when it is discovered upon viewing through the endoscope that the lesion to be treated is larger than was expected.

DESCRIPTION OF THE PREFERRED EMBODIMENT

We first briefly describe the drawings.

Drawings

Structure

Figure 1:
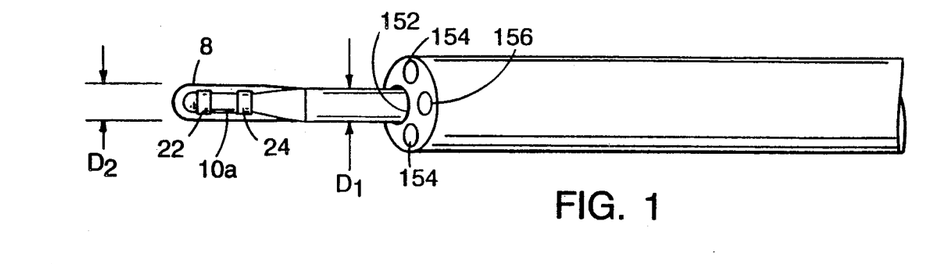
FIG. 1 is a drawing of an endoscope and a balloon catheter according to the invention, the balloon catheter passing through a channel in the endoscope in a deflated condition.
Figures 1A, 1B:
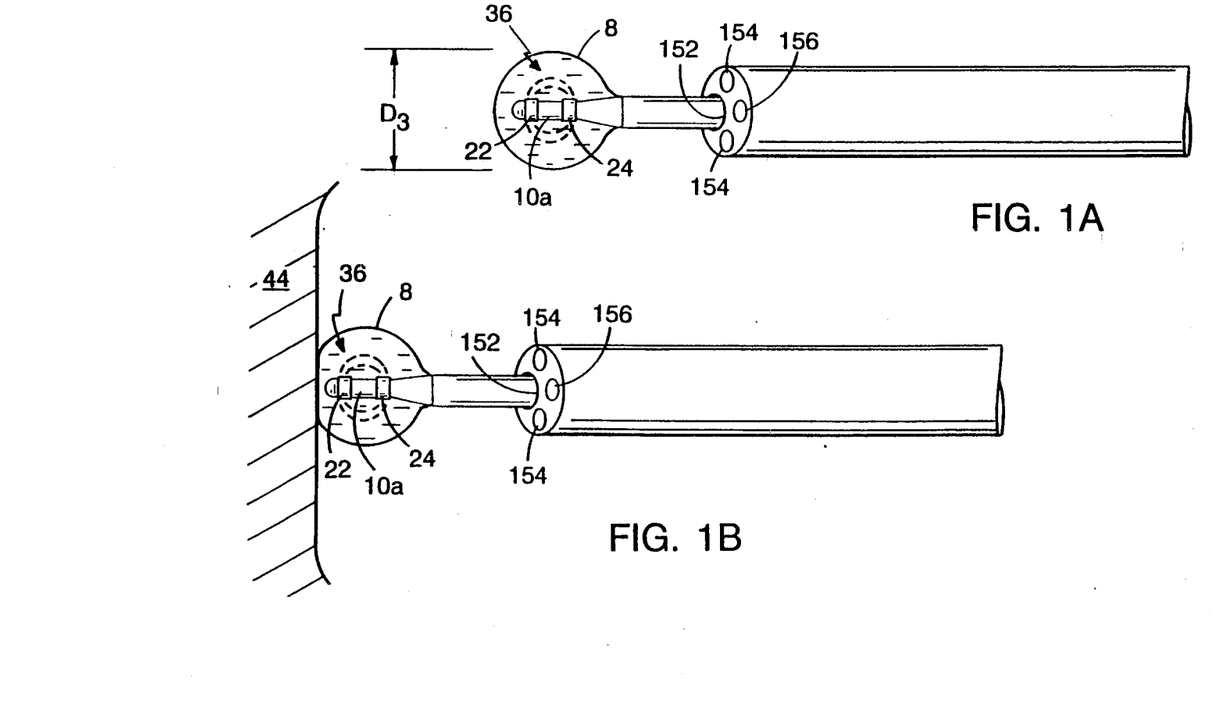
FIG. 1A shows the balloon catheter of FIG. 1 in an inflated condition.
FIG. 1B shows the balloon catheter of FIG. 1 in an inflated condition and pressed against tissue to be treated.

Referring to FIGS. 1, 1A, and 1B, an endoscope 150, which is insertable through a duct in a patient's body, is cylindrical in shape. A pair of light sources 154 and a viewing window 156 are located on the distal end of the endoscope. The endoscope 150 is used for viewing the inside of the patient's body, to determine the location of a lesion such as an ulcer in the stomach, other gastrointestinal bleeding, or bleeding in the lung. A channel passes through the length of the endoscope and terminates in an opening 152 in the distal end of the endoscope. The channel diameter is typically 2.8 millimeters.

A hemostatic balloon probe 34 is insertable through the channel of endoscope 150 when the balloon 8 is deflated, as shown in FIG. 1. The balloon can then be inflated to the shape of a sphere, as shown in FIG. 1A, which can be pressed against tissue either en face, as shown in FIG. 1B, or tangentially. The catheter shaft has a diameter D1 of 5 French, 7 French, or 10 French. The balloon when fully inflated typically has a diameter D3 of approximately three to five millimeters. The ratio of inflated diameter D3 to deflated diameter D2 is typically 2 to 1. In the embodiment shown in FIGS. 1C–1E, the hemostatic balloon probe 34 includes flexible balloon 8 mounted on nylon catheter shaft 10. The balloon 8 is longitudinally expandable over the tip of catheter shaft 10. The balloon 8 may be either an elastic polymer balloon or a foldable, noncompliant dilatation balloon. If the balloon is elastic, it will conform to a lesion and distribute pressure evenly to the zone to be coagulated without leaving gaps between the balloon and the lesion. The balloon may be made of silicon rubber, which is flexible, does not stick, and can accommodate fluid heated to the boiling point of normal saline. Balloon 8 is fillable with an electrically conductive fluid 36 such as normal saline (0.9 percent NaCl in water), a conductive radiopaque fluid, or a mixture of saline solution and a radiopaque fluid. The exterior of the balloon is coated with a non-stick coating having a low coefficient of friction, such as silicone or polysiloxane.

Figure 1C:
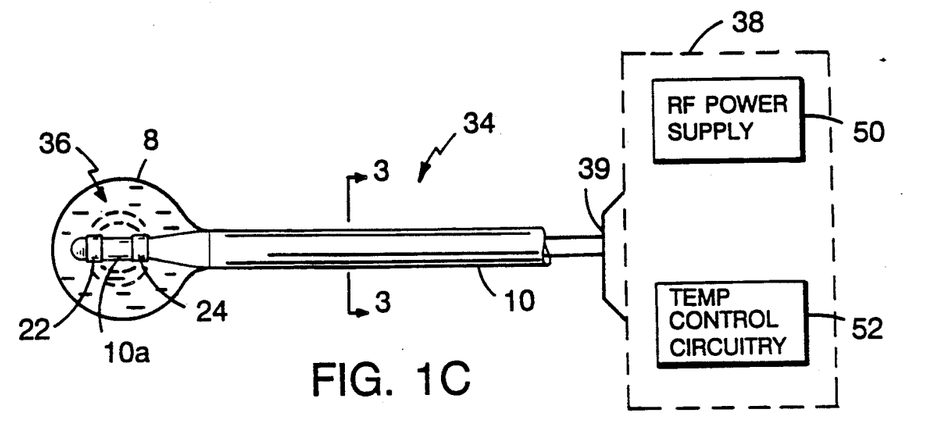
FIG. 1C shows one embodiment of a balloon catheter according to the invention.
Figure 1D:
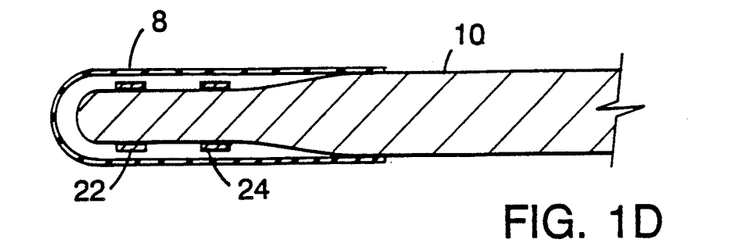
FIG. 1D is a cross-sectional view of the balloon portion of the embodiment of FIG. 1C in a deflated condition.
Figure 1E:
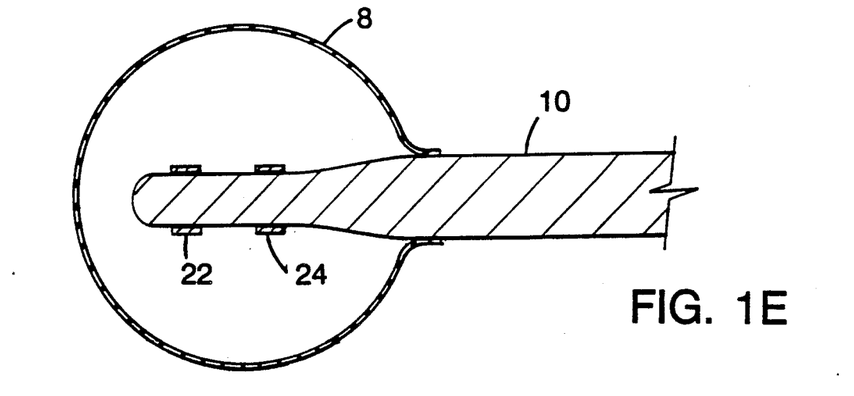
FIG. 1E is a cross-sectional view of the balloon portion of the embodiment of FIG. 1C in an inflated condition.

Annular electrical contacts 22 and 24 inside of balloon 8 have internal diameters matching the portion 10a of the catheter shaft 10 which they surround and are bonded directly to the catheter shaft. The spacing between the contacts is approximately half the length of the inflated balloon, and the spacing from the respective end of the balloon is approximately one fourth the length of the inflated balloon, so that the balloon will heat evenly. While the dimensions of the contacts vary according to the size of the endoscope channel and the nature of the medical procedure to be performed, in this embodiment it is preferable that the contacts be in the form of annular thin-wall bands having their axial length and diameter about equal. For the range of uses contemplated for this embodiment, the inner diameter of the smallest contact is about 0.050 inch, and the inner diameter of the largest contact is about 0.120 inch. The contacts have a radial thickness of approximately 0.002 inch, and therefore present a low profile. The contacts can be made of any conductive material that is compatible with the conductive solution and the conditions of use, but are preferably of a radiopaque metal such as platinum or tantalum, so that they may serve as radiopaque markers during placement of the catheter. Contacts 22 and 24 are preferably coated with tin, so that they may be soldered by means of tin solder to copper wires that extend through the length of the catheter shaft and connect with the contacts at locations immediately beneath the contacts.

RF power supply 50 preferably operates at 650 kilohertz, but can be at any frequency within the range of about 100 kilohertz to 1 megahertz. It is important to use radio frequency power rather than direct or low frequency current, or microwave power, because the risk of a physiological response or electrocution response is reduced at RF frequencies above 100 kHz kilohertz as compared with d.c. or low frequencies, and because microwave power would lead to radiative losses in wires within the catheter shaft 10, that can result, e.g., in unwanted heating of the catheter shaft. The fluid 36, while selected to have resistive losses, has an electrical impedance low enough that it will conduct the current supplied by RF power supply 50 at voltages of about 100 volts or lower. For example, if the current I is set at 1 amp, and the impedance R between the electrodes, through the fluid is 100 ohms, the voltage V will be 100 volts according to V=IR, and the power P dissipated into the fluid will be 100 watts, according to $P = I^2 R$. general, where two electrodes are employed, the impedance between the electrodes will be less than 1000 ohms, preferably in the range of 50 to 500 ohms, and in the present embodiment most preferably at about 100 ohms. In all events the shape of the balloon and the construction and spacing of the electrical contacts are preselected so that the electrical current is substantially confined to the interior of the balloon. The fluid 36 within balloon 8 may be black or dark, so that in addition to the fluid being heated by resistive conductive of RF electric current, the fluid thermally absorbs the RF radiation from the electrodes. A black or dark fluid 36 can therefore heat up more efficiently than a clear fluid or a white fluid.

Catheter 34 plugs into RF power supply and temperature control circuitry 38 by means of a plug 39 that is keyed with respect to the particular size of balloon catheter it is associated with, to cause the power supply to operate at a maximum current of 1/10, ½, ¼ or 1 amp. Plug 39 has seven pins, three of which are needed to operate the catheter. During manufacture, a jumper connection is made within plug 39 between a selected two of the remaining four pins. The jumper connection indicates how much current, at maximum, the RF power supply 50 should produce, depending upon which pins the jumper connection connects. Thus, the user need only select the appropriate catheter 34, and need not be concerned about selecting the appropriate maximum current.

Figure 1F:
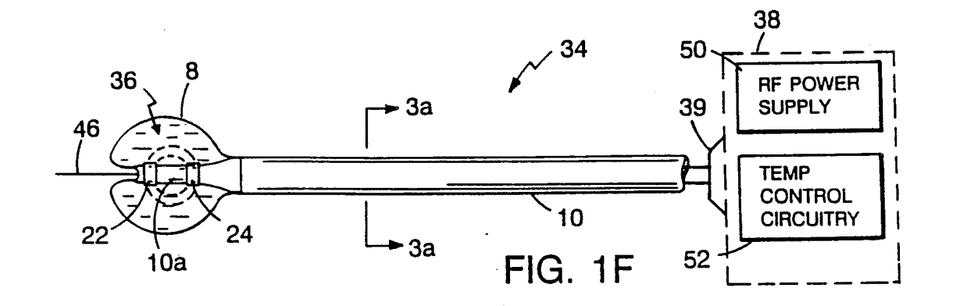
FIG. 1F shows another embodiment of a balloon catheter according to the invention.
Figure 1G:
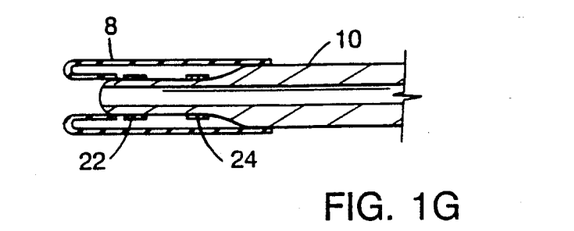
FIG. 1G is a cross-sectional view of the balloon portion of the embodiment of FIG. 1F in a deflated condition.
Figure 1H:
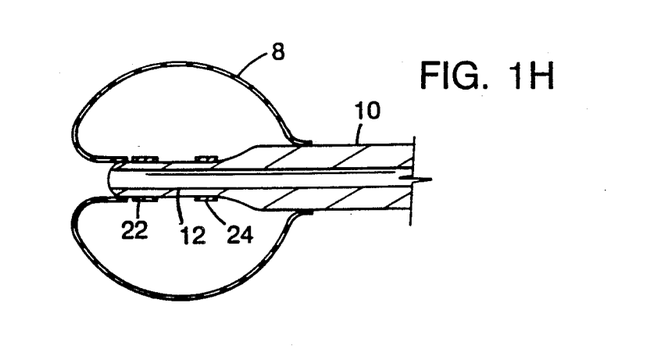
FIG. 1H is a cross-sectional view of the balloon portion of the embodiment of FIG. 1F in an inflated condition.

In the embodiment of FIGS. 1F-1H the catheter shaft has a lumen 12 through its length, which provides a conduit for fluid that is used to wash blood away to enable unobstructed viewing of the lesion. The fluid is preferably water or carbon dioxide. The lumen 12 through the length of the catheter shaft 10 may alternatively provide a conduit for a guidewire 46. The guidewire exits the catheter shaft 10 through an opening 154 in the tip of the catheter shaft. The balloon 8 is arranged annularly around the opening 154 and expands longitudinally beyond the tip of the catheter shaft 10.

Figure 2:
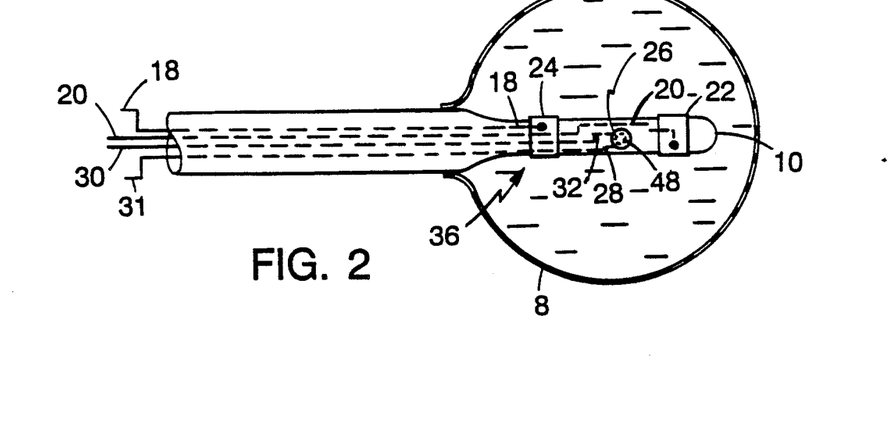
FIG. 2 is a detailed drawing of the balloon portion of the balloon catheter shown in FIG. 1, according to an embodiment of the invention in which a temperature sensing device is mounted inside the balloon.

Referring to FIG. 2, in one embodiment of the invention, a bead thermistor 26, 0.014 inch in diameter and 0.020 inch long, is mounted directly upon catheter shaft 10 between electrodes 22 and 24. Stainless steel thermistor leads 28 and 32 connect thermistor 26 with 34-gauge, multi-filament, TEFLON coated, copper wires 31 and 30 respectively. Wires 31 and 30, which have an outer diameter 0.012 inch, are soldered to the stainless steel thermistor leads 28 and 32, and connect thermistor leads 28 and 32 with RF power supply and temperature control circuitry 38 via the pins of the plug. Thermistor 26 fits snugly on top of an opening 48 in the wall of catheter shaft 10 midway between electrodes 22 and 24. Thermistor leads 28 and 32 and wires 31 and 30 are enclosed within catheter shaft 10, and thermistor leads 28 and 32 connect with thermistor 26 through opening 48. An insulating coating of epoxy or urethane seals thermistor 26 on top of opening 48. Electrodes 22 and 24 are soldered to 34-gauge, multi-filament, copper wires 20 and 18, respectively. These wires, which are TEFLON-insulated, and have outer diameters of 0.012 inch, connect contacts 22 and 24, respectfully to opposite poles of current-controlled (constant current) radiofrequency power supply 50. Wires 20 and 18 are enclosed within catheter shaft 10 along its length, and connect with the contacts at locations immediately beneath the contacts.

Figure 3:
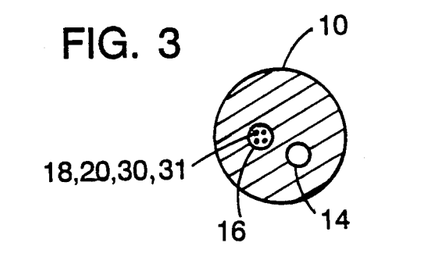
FIG. 3 is a transverse cross-section of the catheter shaft of the balloon catheter shown in FIG. 1C, taken along line 3—3.
Figure 3A:
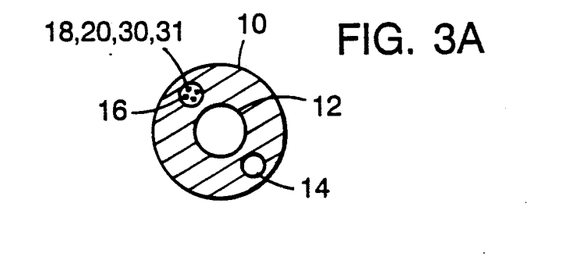
FIG. 3A is a transverse cross-section of the catheter shaft of the balloon catheter shown in FIG. 1F, taken along line 3A—3A.

Referring to FIGS. 3 and 3A, catheter shaft 10 has as many as three lumens 12, 14, and 16. Lumen 12 of FIG. 3A extends from the proximal end of catheter shaft 10 to the distal end, and provides a conduit for guidewire 46 or for washing fluid in the embodiment of the invention shown in FIGS. 1F-1H. Lumen 14 extends from the proximal end of catheter shaft 10 to an outlet in the inside of balloon 8, and provides a conduit for fluid 36 as balloon 8 is inflated and deflated. Lumen 16 extends from the proximal end of catheter shaft 10 to the inside of balloon 8. Lumen 16 provides a conduit for wires 18 and 20, and for wires 31 and 30 which connect with thermistor leads 28 and 32 within lumen 16.

Figure 4:
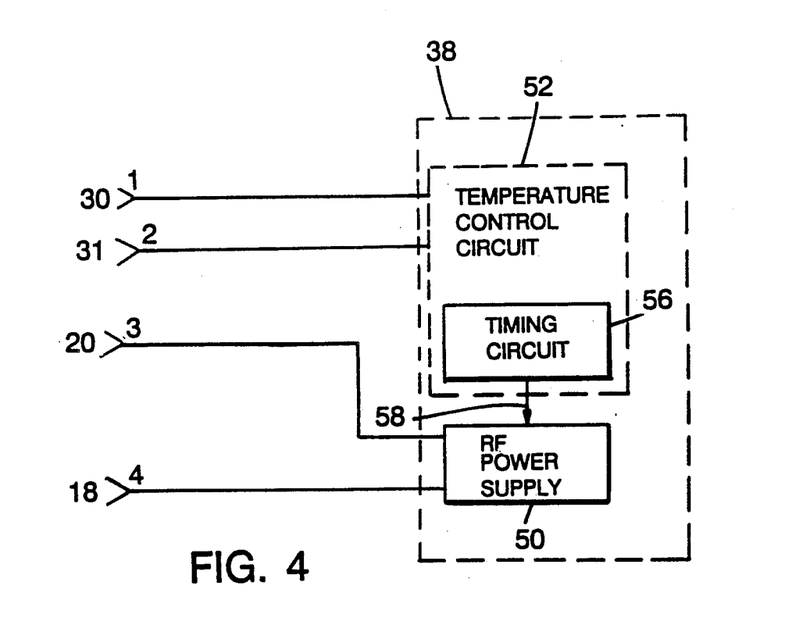
FIG. 4 is a block diagram of the RF power supply and temperature control circuitry according to the embodiment of the invention of FIG. 2.

Referring to FIG. 4, RF power supply and temperature control circuitry 38 consists of RF power supply 50, temperature control circuit 52. Wires 18 and 20 connect electrodes 24 and 22, respectively, with RF power supply 50, and wires 31 and 30 connect thermistor leads 28 and 32 with temperature control circuit 52. Timing circuit 56 of temperature control circuit 52 toggles hold/NOT sample line 58, causing RF power supply 50 to turn on and off for purposes of power application and temperature sensing respectively. The temperature sensing period is 1 percent of the 60 hertz cycle. During the temperature sensing period, temperature control circuit 52 determines how much power, at maximum, RF power supply 50 should supply during the next power application period. By thus time-sharing between temperature sensing and application of current to the electrodes, the temperature control circuitry eliminates the possibility that thermistor 26 will pick up RF noise from the electrodes 22 and 24.

Figure 5:
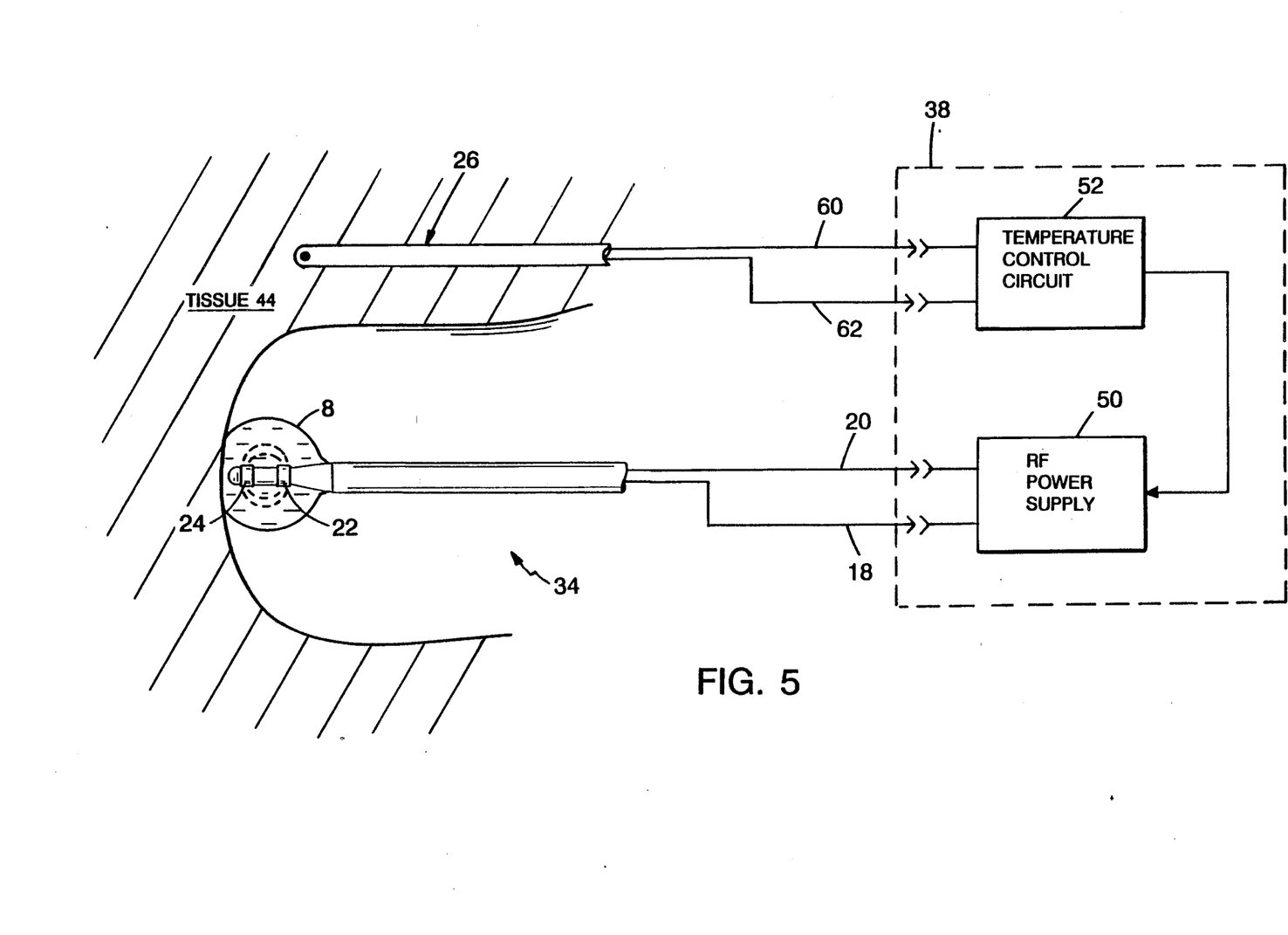
FIG. 5 is a block diagram of the RF power supply and temperature control circuitry according to an embodiment of the invention in which a temperature sensor is placed in direct contact with the tissue surrounding the balloon.

Referring to FIG. 5, another embodiment of the invention is shown in which temperature sensor 26 is placed in direct contact with tissue 44, outside of balloon catheter 34. Wires 60 and 62 connect temperature sensor 26 with temperature control circuit 52, and wires 20 and 18 connect electrodes 22 and 24 respectively with RF power supply 50. Temperature control circuit 52 regulates RF power supply 50 in response to the input from temperature sensor 26.

Figure 6:
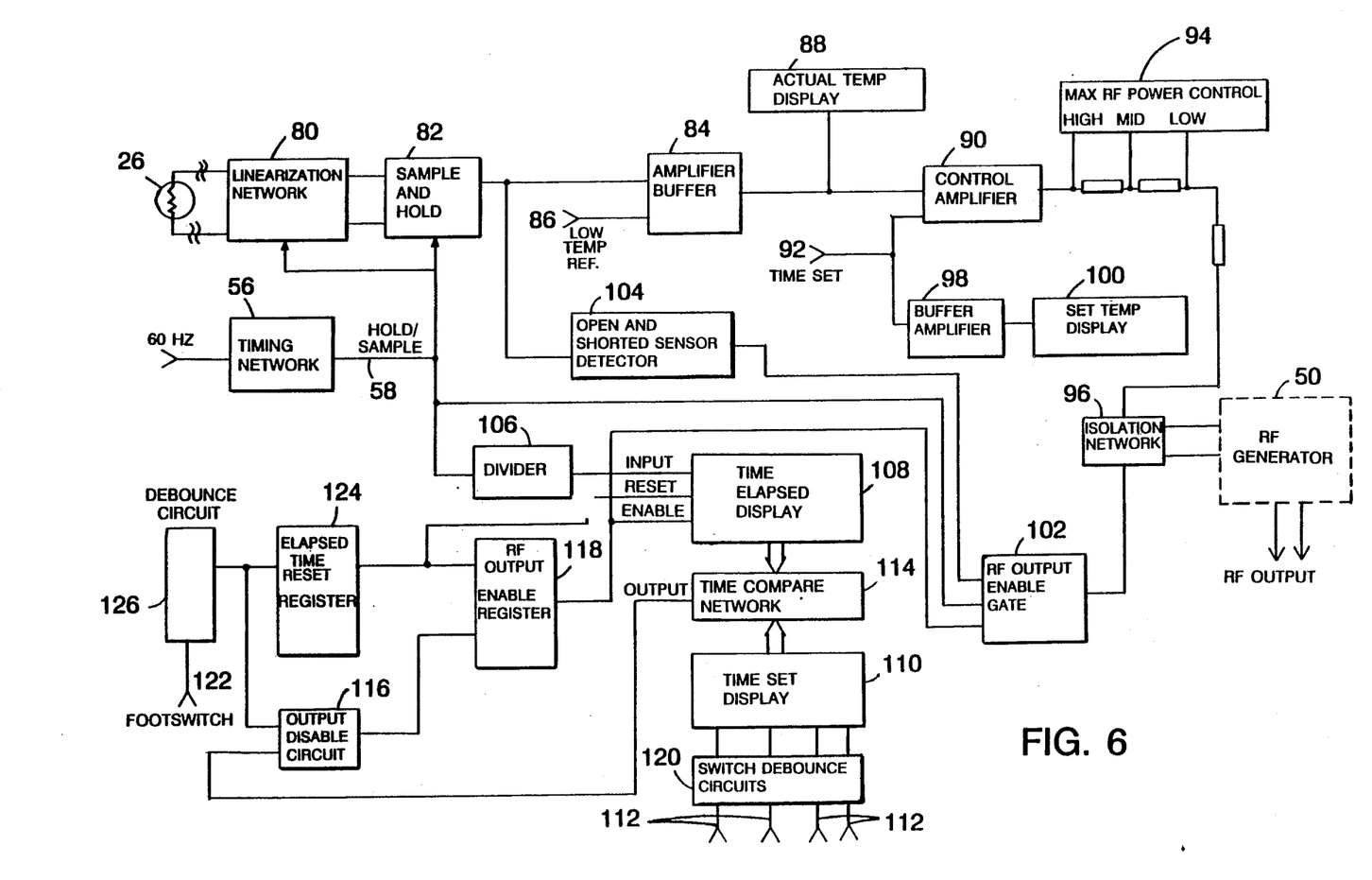
FIG. 6 is a detailed block diagram of the temperature control circuit shown in FIGS. 4 and 5.

Referring to FIG. 6, in temperature control circuit 52, linearization network 80 linearizes the input signal from temperature sensor 26 and delivers the linearized signal to sample and hold register 82. The signal is delivered to amplifier buffer 84 having low-temperature reference 86. Actual temperature display circuit 88 displays the output of amplifier buffer 84. Control amplifier 90 compares the output of amplifier buffer 84 with a temperature set voltage 92 that is set by the user. The maximum RF power control circuit 94 receives the output of control amplifier 90 and determines the level of RF power, at maximum, that the RF power supply 50 should produce. The signal from the maximum RF power control circuit 94 is received by isolation network 96, which interfaces with RF power supply 50. The temperature set voltage 92 is received by buffer amplifier 98 and displayed by set temperature display 100.

Timing circuit 56 toggles hold/NOT sample line 58 at 60 hertz. Hold/NOT sample line 58 is low during 1 percent of the cycle and high during the other 99 percent of the cycle. Hold/NOT sample line 58 is low when signals from temperature sensor 26 are being sampled and high when signals from temperature sensor 26 are not being sampled. Hold/NOT sample line 58 is received by RF output enable gate 102. The output of sample and hold register 82 is processed by open and short sensor detector 104 to determine whether a sensor malfunction, such as a shorted or open sensor, has occurred. The output of open and shorted sensor detector 104 is received by RF output enable gate 102. RF output enable gate 102 delivers a signal to isolation network 96, which turns off RF power supply 50 when there has been a sensor malfunction or when signals from temperature sensor 26 are being sampled.

Divider 106 receives hold/NOT sample line 58 and delivers its output to time elapsed display 108. Time set display 110 displays the time indicated by time set switches 112, which are set by the user. Time compare network 114 compares the elapsed time with the time set by the user, and delivers an output signal to output disable circuit 116. The output of output disable circuit 116, which is active only when the elapsed time is less than the time set by the user, is delivered to RF output enable register 118. RF output enable register 118 in turn delivers the signal to the enable input to time elapsed display 108, and also to RF output enable gate 102, so that RF power supply 50 may be turned off when the time set by the user has elapsed. Switch debounce circuits 120 are provided for time set switches 112.

The user must depress footswitch 122 in order for RF power supply 50 to operate. While footswitch 122 is activated, and while the elapsed time is less than the time set by the user, output disable circuit 116 delivers a signal to RF output enable register 118, which in turn delivers the signal to the enable input of time elapsed display 108, and also to RF output enable gate 102 so that RF power supply 50 may be turned on. Deactivation of footswitch 122 causes a signal to pass through elapsed time reset register 124, in order to reset time elapsed display 108 and in order to reset RF output enable register 118. The resetting of RF output enable register 118 causes RF output enable gate 102 to turn off RF power supply 50. Debounce circuit 126 is provided for footswitch 122.

Operation

Referring to Figure 1, endoscope 150 is insertable through a duct in a patient's body. Once the endoscope has been inserted into the patient's body, it is used for viewing the inside of internal organs such as the stomach, other parts of the gastrointestinal system, the lung, etc., to determine the location of a bleeding lesion. The user then preselects the desired therapeutic temperature (temperature set voltage 92, FIG. 6), which is typically 105° C. to 110° C. (the boiling point of saline, which is sufficient to cause coagulation of blood), and sets the length of time for which balloon 8 is to be heated (time set switches 112, FIG. 6). If the fluid within balloon 8 is allowed to boil, the boiling ensures that the temperature of the fluid is homogenous.

The hemostatic probe 34, with the balloon 8 in its deflated state, is inserted through the channel 152 that passes the length of the endoscope. (In the embodiment of FIGS. 1F-1H, a guidewire 46 may first be inserted through the channel 152, and then the hemostatic probe 34 is inserted through the channel over the guidewire.) The balloon 8 is positioned beyond the distal end of the endoscope. Balloon 8 is inflated through lumen 14 with either saline, a conductive radiopaque fluid, or a mixture of saline and a radiopaque fluid. The balloon is placed en face against the lesion to be treated, and is pressed against the lesion. The portion of the catheter shaft within the balloon may press against the wall of the balloon as the balloon presses against the tissue, thereby providing support for the balloon. The pressure of the balloon against the tissue causes closing of capillaries, which minimizes the ability of the tissue to act as a heat sink. Thus, the temperature of the fluid inside the balloon, which is the temperature sensed by the transducer 26, closely approximates the temperature of the tissue, which is the temperature of actual significance.

The user depresses footswitch 122 (FIG. 6) to initiate the bi-polar heating between the electrodes 36. Heat is dissipated into the pressurized fluid according to the formula $P = I^2 R$ where P is the power that is dissipated into the fluid, I is the current that is passed through the electrodes, and R is the resistance of the fluid. If the balloon has a diameter of 4 millimeters the fluid will begin to boil locally in about 5 seconds. The heat from the fluid is conducted across the balloon wall into the surrounding tissue 44. Heating will continue until the time set by the user has elapsed, or until the user deactivates footswitch 122.

The combination of heat and pressure causes coagulation of the lesion. The coagulation zone is not limited to the size of the hemostatic probe or the diameter of the endoscope channel. Because the balloon expands to a diameter greater than the diameter of the transverse cross-section of the endoscope channel, it is not necessary to preselect an endoscope having a large diameter, or to switch to a larger endoscope when it is discovered that the zone to be heated is large. Moreover, since the balloon heats a large area, it is not necessary to reposition the balloon at multiple locations to ensure that the entire lesion is heated.

Other embodiments are within the following claims. For example, if it is not practicable to place the balloon en face against the tissue to be treated, the balloon need not be longitudinally expandable beyond the tip of the catheter shaft, but may instead be located anywhere along the length of the catheter shaft. The balloon can thus be applied against the tissue to the side rather than in the axial direction.

What is claimed is:

1. An endoscopically introducible, heatable probe, for engagement with and heating treatment of body tissue on the basis of thermal conduction, said probe being sized and constructed for insertion into the body of a patient through a working channel of an endoscope, the channel having a transverse cross-section of a predetermined diameter, said probe comprising a catheter shaft defining a liquid filling lumen, means at the distal end of said catheter shaft defining a thin-walled, collapsible liquid inflatable chamber in liquid receiving relationship with said filling lumen, said catheter, with the chamber-defining wall in collapsed condition, being sized to pass through said predetermined channel of said endoscope, said chamber having an inflated diameter that is greater than the diameter of the transverse cross-section of said endoscope channel, and heating means operable through said endoscope to maintain inflation liquid in said inflated chamber beyond the end of said endoscope at a predetermined elevated tissue-treating temperature, whereby said probe, when said chamber is deflated, can be inserted into said body through said endoscope and thereafter said chamber can be inflated with liquid, said liquid can be heated, and said chamber beyond the end of said endoscope can be pressed against tissue to treat a large area of said tissue relative to the size of said working channel of said endoscope.

2. The endoscopically introducible probe of claim 1 wherein said heating means comprises a heating device located within said chamber for causing electrical current to flow through said liquid within said chamber to heat said liquid on the basis of $I^2R$ losses of said electrical current flowing through said liquid, said liquid in turn heating surrounding tissue by thermal conduction through said wall of said chamber.

3. The endoscopically introducible probe of claim 2 wherein said heating device comprises a plurality of spaced electrical contacts enclosed within said chamber and exposed to said fluid within said chamber, and said heating means further comprises a corresponding plurality of conductors for connecting said electrical contacts to a power supply for applying a radio frequency electrical potential to said contacts, said liquid is an electrically conductive liquid preselected to produce resistive heating, said radio frequency electrical potential causes current to flow through said liquid between said contacts, and said chamber and said contacts are cooperatively constructed and arranged to cause said current to be substantially confined to liquid within said chamber, whereby, on the basis of $I^2R$ losses of said radio frequency electrical current flowing between said electrical contacts, said liquid is heated, and said liquid in turn heats said surrounding tissue by thermal conduction through wall of said chamber.

4. An endoscopically introducible, hemostatic probe for engagement with and heating treatment of body tissue on the basis of thermal conduction, said probe sized and constructed of insertion into the body of a patient through a working channel of an endoscope, the channel having a transverse cross-section of a predetermined diameter, said hemostatic probe comprising a catheter shaft defining a liquid filling lumen, means at the distal end of said catheter shaft defining a thin-walled, collapsible liquid inflatable chamber in liquid receiving relationship with said filling lumen, said chamber having a diameter when inflated that is greater than the diameter of the transverse cross-section of the endoscope channel, said catheter, with said chamber-defining walls in collapsed condition, being sized to pass through said predetermined channel of said endoscope, said chamber when inflated extending axially beyond the distal end of the catheter shaft, and heating means operable through said endoscope to maintain inflation liquid in said inflated chamber beyond the end of said endoscope at a predetermined temperature sufficient to cause coagulation in tissue surrounding said chamber, said heating means comprising a heating device located within the chamber for causing electrical current to flow through the liquid within the chamber to heat the liquid on the basis of $I^2R$ losses of the electrical current flowing through the liquid, the liquid in turn heating surrounding tissue by thermal conduction through the wall of the chamber, whereby said probe, when said chamber is deflated, can be inserted into said body through said working channel and thereafter said chamber can be inflated with liquid, said liquid can be heated, and said chamber beyond the end of said endoscope can be pressed against tissue to treat a large area of said tissue relative to the size of the working channel of the endoscope.

5. The endoscopically introducible, hemostatic probe of claim 4 wherein the predetermined temperature sufficient to cause coagulation is a boiling temperature of said liquid within said chamber.

6. The endoscopically introducible probe of claim 1 or 4 wherein said wall of said chamber comprises an elastic balloon.

7. The endoscopically introducible probe of claim 1 or 4 wherein said wall of said chamber comprises a foldable, substantially noncompliant balloon.

8. The endoscopically introducible probe of claim 1 or 4 wherein said wall of said chamber comprises a balloon that surrounds the distal end of said catheter shaft.

9. The endoscopically introducible probe of claim 1 or 4 wherein said catheter shaft defines a second lumen extending through said catheter shaft and terminating at an opening in a distal end of said catheter shaft, and said chamber comprises a balloon that is disposed annularly around the distal portion of said catheter shaft in a manner such that, when filled with said liquid, said chamber extends distally beyond the end of said catheter shaft.

10. The endoscopically introducible probe of claim 9, further comprising a guidewire for facilitating introduction of said catheter shaft through said channel of said endoscope, the guidewire passing through said second lumen of said catheter shaft.

11. An endoscopically introducible, heatable probe for engagement with and heating treatment of body tissue on the basis of thermal conduction, said probe comprising a catheter shaft defining a liquid filling lumen, means at the distal end of said catheter shaft defining a thin-walled, collapsible liquid inflatable chamber in liquid receiving relationship with said filling lumen, said chamber surrounding the distal end of said catheter shaft, and a heating device located within said chamber for causing electrical current to flow through said liquid within said chamber to heat said liquid on the basis of $I^2R$ losses of said electrical current flowing through said liquid, said liquid in turn heating surrounding tissue by thermal conduction through said wall of said chamber, said heating device comprising a plurality of spaced electrical contacts enclosed within said chamber and exposed to said fluid within said chamber, and said heating means further comprising a corresponding plurality of conductors for connecting said electrical contacts to a power supply for applying a radio frequency electrical potential to said contacts, said liquid being an electrically conductive liquid preselected to produce resistive heating, said radio frequency electrical potential causing current to flow through said liquid between said contacts, and said chamber and said contacts being cooperatively constructed and arranged to cause said current to be substantially confined to liquid within said chamber, whereby, on the basis of I²R losses of said radio frequency electrical current flowing between said electrical contacts, said liquid is heated, and said liquid in turn heats said surrounding tissue by thermal conduction through a wall of said chamber.

12. An endoscopically introducible, heatable probe for engagement with and heating treatment of body tissue on the basis of thermal conduction, said probe comprising a catheter shaft defining a liquid filling lumen, and further defining a second lumen extending through said catheter shaft and terminating at an opening in a distal end of said catheter shaft, means at the distal end of said catheter shaft defining a thin-walled, collapsible liquid inflatable chamber in liquid receiving relationship with said filling lumen, said chamber being disposed annularly around the distal portion of said catheter shaft in a manner such that, when filled with said liquid, said chamber extends distally beyond the end of said catheter shaft, and a heating device located within said chamber for causing electrical current to flow through said liquid within said chamber to heat said liquid on the basis of I²R losses of said electrical current flowing through said liquid, said liquid in turn heating surrounding tissue by thermal conduction through said wall of said chamber, said heating device comprising a plurality of spaced electrical contacts enclosed within said chamber and exposed to said fluid within said chamber, and said heating means further comprising a corresponding plurality of conductors for connecting said electrical contacts to a power supply for applying a radio frequency electrical potential to said contacts, said liquid being an electrically conductive liquid preselected to produce resistive heating, said radio frequency electrical potential causing current to flow through said liquid between said contacts, and said chamber and said contacts being cooperatively constructed and arranged to cause said current to be substantially confined to liquid within said chamber.

whereby, on the basis of I²R losses of said radio frequency electrical current flowing between said electrical contacts, said liquid is heated, and said liquid in turn heats said surrounding tissue by thermal conduction through a wall of said chamber.

13. A method of treating tissue inside a patient's body, comprising the steps of inserting an endoscope into a patient's body, said endoscope having a working channel that passes through said endoscope and that terminates at an opening in a distal end of said endoscope, the channel having a transverse cross-section of a predetermined diameter, viewing the inside of the patient's body through said endoscope, to determine the location of tissue to be treated, positioning a catheter shaft within said channel in a manner such that a portion of said catheter shaft extends beyond said opening in the distal end of said endoscope, a chamber being mounted on said portion of said catheter shaft that extends beyond said opening in the distal end of said endoscope, said chamber being defined by a flexible wall, filling said chamber with fluid, said chamber when filled with fluid having a diameter greater than the diameter of the transverse cross-section of the endoscope channel, positioning said chamber at a location of tissue to be treated, and heating, by means extending through said endoscope, said fluid within said chamber, said fluid in turn heating surrounding tissue by thermal conduction through a wall of said chamber.

14. The method of claim 13, wherein when said chamber is filled with fluid, said chamber extends axially beyond a distal end of said catheter shaft.

15. The method of claim 14, wherein the step of positioning said chamber at the location of tissue to be treated comprises directing said chamber in an axial direction to the location of the tissue to be treated.

16. The method of claim 14, wherein the step of positioning said chamber at the location of tissue to be treated comprises directing said chamber in a tangential direction to the location of the tissue to be treated.

17. The method of claim 14, wherein said chamber surrounds the distal end of said catheter shaft.

18. The method of claim 14, wherein said catheter shaft defines a lumen extending through said catheter shaft and terminating at an opening in the distal end of said catheter shaft, said chamber is disposed annularly around said opening in the distal end of said catheter shaft, and the step of inserting said catheter shaft into said channel comprises the steps of inserting a guidewire into said channel of said endoscope, and inserting said lumen of said catheter shaft over said guidewire, said guidewire facilitating introduction of said catheter shaft through said channel of said endoscope.

19. The method of claim 13, further comprising the step of applying pressure to the tissue as the tissue is heated, so that the tissue is compressed, thereby minimizing heat sinking of the tissue.

* * * * *

UNITED STATES PATENT AND TRADEMARK OFFICE
CERTIFICATE OF CORRECTION

PATENT NO.  : 5,103,804

DATED       : April 14, 1992

INVENTOR(S) : John E. Abele et al.

It is certified that error appears in the above-identified patent and that said Letters Patent is hereby corrected as shown below:

On the title page, items:

[75] Inventors:   "Charles E. Lennox" should be --Charles D. Lennox--;

[56] References Cited:   "4,648,893" should be --4,648,892--;

[56] References Cited:   "Hilterbrandt" should be --Hiltebrandt--;

[56] References Cited:   "Lennex" should be --Lennox--;

OTHER PUBLICATIONS:

Ward Reference, "Alan R. Lisa" should be --Alan R. Liss--;

"Zeither et al." should be --Zeiher et al.--;

Col. 4, line 65, before "general" insert --In--;

Col. 9, line 32, before "wall" insert --a--.

Signed and Sealed this

Ninth Day of November, 1993

*Attest:*

BRUCE LEHMAN

*Attesting Officer*    Commissioner of Patents and Trademarks